United States Patent [19]

Williams

[11] 4,247,362

[45] Jan. 27, 1981

[54] HIGH YIELD FIBER SHEETS

[75] Inventor: James C. Williams, Memphis, Tenn.

[73] Assignee: The Buckeye Cellulose Corporation, Cincinnati, Ohio

[21] Appl. No.: 41,043

[22] Filed: May 21, 1979

[51] Int. Cl.$^3$ .................. D21C 3/06; D21H 5/14; D04H 1/20

[52] U.S. Cl. ..................... 162/13; 162/28; 162/83; 162/141; 162/201; 264/121

[58] Field of Search .............. 162/13, 23–28, 162/83, 100, 141, 142, 150, 159, 201, 17, 64; 264/121

[56] References Cited

U.S. PATENT DOCUMENTS

| | | | |
|---|---|---|---|
| 1,920,496 | 8/1933 | Carpenter | 162/141 |
| 2,131,097 | 9/1938 | Drewsen | 162/141 |
| 2,325,055 | 7/1943 | Heritage | 162/159 |
| 3,388,037 | 6/1968 | Asplund et al. | 162/26 |
| 3,591,450 | 7/1971 | Murphy et al. | 162/28 |
| 4,065,347 | 12/1977 | Aberg et al. | 162/26 |
| 4,116,758 | 9/1978 | Ford et al. | 162/28 |
| 4,120,747 | 10/1978 | Sarge et al. | 162/142 |
| 4,145,246 | 3/1979 | Goheen et al. | 162/28 |
| 4,152,197 | 5/1979 | Lindahl et al. | 162/28 |

*Primary Examiner*—Peter Chin
*Attorney, Agent, or Firm*—Monte D. Witte; John V. Gorman; Richard C. Witte

[57] ABSTRACT

Wet-laid sheets of softwood high yield fibers in combination with hardwood high yield fibers. The sheets, which are strong enough to be handled by commercial equipment, are formed on conventional papermaking machines using a furnish comprising a major proportion of softwood high yield fibers in admixture with a minor proportion of hardwood high yield fibers. The hardwood high yield fibers are specially prepared by a procedure comprising treating hardwood with relatively high levels of chemicals under relative stringent conditions and defibrating the treated hardwood with relatively high levels of power input. Airfelts made from these sheets exhibit low wet densities. Processes for making the sheets and the airfelts are also provided.

18 Claims, No Drawings

HIGH YIELD FIBER SHEETS

TECHNICAL FIELD OF THE INVENTION

This invention relates to wet laid sheets of high yield wood pulp fibers, which sheets are prepared on conventional paper-making machines, and to air-laid, non-woven webs which are subsequently made from these sheets of high yield wood pulp fibers.

BACKGROUND ART

Absorbent articles such as disposable diapers, sanitary napkins, and the like, manufactured from wood pulp have become staple items of commerce. Heretofore, these items have been primarily made from chemical pulp (e.g. wood pulp made by the sulfite process or by the kraft process). While these absorbent articles have been of good quality, the use of chemical pulp offers certain disadvantages. One major disadvantage is inherent in the chemical pulping process itself. Only about 50% of the wood entering the chemical pulping process is recovered as pulp. The remaining fraction of the wood, as well as the concentrated chemicals used in the pulping process, contribute to both atmospheric and ground water pollution unless expensive steps are taken to control plant emissions. Another disadvantage of the use of chemical pulp in absorbent articles is the relatively low bulk of the chemical pulp. (Bulk, the reciprocal of density, is a measure of the ability of wood pulp to make a product of low inherent density.) Wood pulps having high bulks make products with low densities. Since absorbency is inversely related to density, products with low densities are more absorbent on a weight basis than are products with high densities. The use of a wood pulp with higher bulk allows the manufacture of a product having relatively greater absorptive capacity on an equal weight basis than a similar product made from wood pulp with lower bulk. Alternatively, on an equal absorptive capacity basis, products made from a wood pulp with higher bulk will contain a smaller quantity of fiber than a product made from wood pulp with lower bulk.)

In more recent times, these two described disadvantages have been at least partially overcome through the use of high yield fiber. As used herein, the term "high yield fiber" denotes a wood pulp which is made by a process which allows significantly more of the entering wood to be recovered as wood pulp fiber than do the conventional sulfite or kraft pulping processes. High yield fibers are classified into numerous different types.

One of the oldest and most widespread high yield fibers is known as groundwood. It is produced by mechanically reducing the wood to fibers as by pressing the wood against a rotating stone. Groundwood, which is sometimes known by the generic term mechanical pulp, has found little application in absorbent articles such as diapers because this method of fiber separation leads to significant fiber shortening and damage before a reasonably low level of fiber bundles, i.e. shieves, is obtained.

Another form of mechanical pulp which has found somewhat greater use in absorbent products is broadly known as thermomechanical pulp. Thermomechanical pulp, which is generally attributed to the work of Asplund and his coworkers as described in U.S. Pat. No. 2,008,892 (July 23, 1935) and its progeny, involves the mechanical defibration of wood after the lignin has been softened by steaming.

Semi-chemical pulp, sometimes known as chemimechanical pulp, or semi-mechanical pulp, is a refinement of the basic thermomechanical process. Here, wood chips are given a mild chemical treatment during a heating step prior to mechanical difibration in a device such as a rotating disc defibrator. The chemical treatment is limited so as to merely soften the lignin rather than completely remove it as in conventional chemical pulping processes. Workers such as Beverage and Keough in U.S. Pat. No. 2,422,522 (June 17, 1947), Beverage, Keough and Surino in U.S. Pat. No. 2,425,024 (Aug. 5, 1947) and Asplund, Cederquist and Reinhall in U.S. Pat. No. 3,338,525 (Aug. 29, 1967) have described semi-chemical high yield fiber processes.

Also within the prior art is a semi-chemical high yield fiber process which yields a product having relatively high bulk and a relatively low shieve content. This particular process comprises the steps of preheating wood chips, treating the heated chips with a chemical solution which comprises sodium sulfite and, optionally, basic chemicals, at such a concentration as to yield pulp having a pH greater than 5.7. The chips are then mechanically defibrated to pulp with an energy consumption of less than about 600 kilowatt hours per metric of pulp produced. (Anonymous, Research Disclosures, March, 1978, p. 20.)

Generally speaking, following the pulping operation high yield fibers are formed into sheets by any of several well known wet forming processes typified by the conventional Fourdrinier process. (The operation of forming the wood pulp fibers into sheets is sometimes known as lapping.) The sheets are then usually dried with conventional equipment. For use in absorbent products such as diapers, the sheets are comminuted and the high yield fibers are formed into absorbent products known as airfelts.

The high yield fibers most preferred for use in absorbent products such as diapers are generally derived from softwoods (gymosperms). One of the problems associated with the use of these softwood high yield fibers in absorbent products heretofore has been the weakness of the sheets of pulp fibers. These sheets must be strong enough to be handled by commercial equipment during the airfelt making process, but sheets of the preferred softwood high yield fibers are generally too weak to be used as is. In fact, it is impossible to form sheets at all from some of the most preferred softwood high yield fibers.

One way the strength of the sheets has been improved has been by mechanically refining the fibers. This operation, which is known to increase strength in almost all papermaking areas, suffers from the disadvantages of increased cost and those effects which flow from the mechanical damage to fibers caused by the refining process, e.g. increased fines, lowered drainage rate, increased density, lowered absorbency. Refining is not, however, necessarily effective with all softwood high yield fibers.

Sheet strength has also been improved by adding a quantity of chemical pulp to the softwood high yield fibers. Chemical pulp, which may comprise up to 25% or more of the total pulp mixture, can optionally be refined in the wet state prior to its addition to the pulp blend. While the addition of chemical pulp does increase the strength of the wet laid sheets of softwood high yield fibers, certain adverse effects do occur. One of the most readily apparent, of course, is the increased cost of the total fiber mixture which results from the replacement of relatively low cost high yield fiber with relatively high cost chemical fiber. A second, more subtle adverse effect is the increase in wet density of the airfelt which results when chemical fibers are blended with the softwood high yield fibers.

High yield fibers are essentially non-delignified; that is, most of the lignin remains with the cellulosic fiber. This lignin contributes to the stiffness of the fiber. It has been found that these stiff fibers form airfelts having lower wet density than do conventional chemical pulp fibers. That is, if equivalent airfelts are formed from chemical pulp fibers and from stiff, non-delignified, high yield fibers, and the airfelts are compressed dry to the same initial density, the high yield fiber airfelts exhibit lower density when wet and under load than do the chemical pulp fiber airfelts.

Although Scott, in U.S. Pat. No. 2,642,359 (June 16, 1953) has suggested that the strength of a pulp sheet can be enhanced by incorporating into the fiber furnish from which the sheet is made a quantity of short fibers which tend to bind together long fibers, it is well known in the art that hardwood high yield fibers (which are generally shorter than softwood fibers) contribute to the weakness of sheets of fibers.

There are basic anatomical differences between softwoods and hardwoods. The arbitrary term softwood and hardwood designate, respectively, trees having needle or scalelike leaves and trees having broad leaves which are deciduous in temperate zones. The hardness or density of the wood is not involved. While there are differences between the chemical structures of hardwood and softwoods, the important difference, for this invention, lies in the variation in cell structure. Softwoods for the most part are made up of cells whose length is several hundred times their diameter. That is, even though barely visible to the eye, they are threadlike. Hardwoods, on the other hand, are made up of a wider variety of cell types characterized by a length to diameter ratio which may run from 1:1 to 20:1. Hardwood fiber is generally considered to be inferior to softwood fiber for certain applications. Because its ratio of length to diameter is so much smaller, the bonding between fibers is poorer because the inter-fiber crossings per fiber are fewer and the bond area of each is smaller. Consequently, a sheet is generally weaker when it contains hardwood fibers. Generally commented on the lower strength properties of hardwood sheets relative to softwood sheets in a paper entitled "Poplar Groundwood in Different Grades of Paper" delivered the EUCEPA Symposium on Mechanical Pulp held in Oslo, Norway during June, 1970, as reported in the Abstract Bulletin of the Institute of Paper Chemistry, Vol. 42, No. 3, Abstract No. 2647 (September, 1971).

DISCLOSURE OF THE INVENTION

This invention concerns sheets of softwood high yield fibers which have adequate strength for commercial usage and which have been formed by wet-laying techniques. Adequate strength is obtained by blending with the softwood high yield fibers a quantity of hardwood high yield fibers which have been specially prepared. The special preparation comprises treating hardwood chips with relatively high levels of chemicals for relatively long periods of time and defibrating the chips with relatively high power input. The blended fibers are formed into sheets by conventional processes. The sheets are then used in the manufacture of airfelts made by other conventional processes.

Accordingly, it is an object of this invention to provide dry sheets of wood pulp fibers, said sheets having adequate strength for commercial processing.

It is an object of this invention to provide sheets comprised of relatively undamaged, substantially non-delignified, softwood high yield fibers, said sheets having adequate strength for commercial usage.

It is an object of this invention to provide airfelts having improved wet density properties.

It is a further object of this invention to provide a process for preparing the above-mentioned sheets of fibers.

It is a still further object of this invention to provide a process for preparing the above-mentioned airfelts.

These and other objects will become readily apparent from a reading of the Detailed Description of the Invention which follows.

DETAILED DESCRIPTION OF THE INVENTION

While this specification concludes with claims particularly pointing out and distinctly claiming the subject matter regarded as the invention, it is believed that the invention will be better understood through a reading of the following detailed description of it and of the non-limiting example appended thereto.

This invention is directed not only to the production of dried sheets comprised totally or substantially of high yield fibers and to the production of airfelts from such sheets, but also to the dried sheets of fibers and to the airfelts per se. The invention can best be described, however, in terms of several distinct process operations.

The improved sheets of this invention are comprised primarily of high yield fibers derived from softwoods (gymosperms). Any of the softwood species commonly used for making paper pulp can be used. Suitable species include *Picea glauca* (white spruce), *Picea mariana* (black spruce), *Picea rubra* (red spruce), *Pinus strobus* (white pine), *Pinus caribeau* (slash pine), and *Pinus tadea* (loblolly pine). The last named species is a preferred one for use in this invention.

Processes for converting softwoods to high yield fiber pulps are relatively well known in the art. The one described in the following paragraphs can be used advantageously in the practice of this invention, but this invention is not to be considered limited to the use of this process.

Softwood trees are reduced to chips and the chips are optionally washed using equipment and processes common in the pulp industry. The washed chips are held in storage bins until they are needed in the pulping process.

The pulping process begins when the washed wood chips are removed from the chip storage bin and are conveyed by any suitable means to a presteamer. In the presteamer, the temperature of the chips is raised from ambient up to any desired level below about 99° C. by the introduction of steam. The purpose of the presteamer, which can be any suitable vessel, is to raise the temperature of the chips and expell much of the air associated with them.

From the presteamer, the chips are conveyed to a treatment unit. A suitable conveying device is a screw conveyor, optionally tapered, which tends to compress the chips. Not only does such a device move the chips and seal the treatment unit against pressure loss, but it also materially aids in the impregnation of chips during the treating step. The chips which have been compressed in the screw conveyor are discharged in that compressed condition into the treatment unit below the surface of the treatment liquor contained therein. When the mechanical pressure on the chips is reduced as the chips are introduced into the treatment unit, the chips expand and absorb treatment liquor.

During the treating step performed in the treatment unit, the chips are impregnated with treatment liquor and are maintained at elevated temperature and pressure for a prescribed length of time.

A suitable treatment unit comprises two elements: an impregnator and a retention chamber. The impregnator preferably comprises a cylindrical vessel oriented with its axis vertical. This cylindrical vessel is provided with a first means adapted for the introduction of treatment liquor into the impregnator and with a second means adapted for the moving of chips vertically through the cylindrical vessel to a point where they are allowed to exit the vessel. The first means can be any arrangement of valves and piping the specification of which is well within the ability of one skilled in the art. Provision of a region equivalent to a pool of treatment liquor within the impregnator is desirable. The second means can be a vertically oriented screw conveyor.

Preferably, the impregnator is contained within a larger pressurized outer vessel wherein elevated pressure and temperature are maintained by the introduction of steam. The impregnator is preferably situated in the upper regions of this pressurized outer vessel and a portion of the lower regions provides a retention chamber. After exiting the impregnator, the chips and the treatment liquor associated therewith are allowed to fall by gravity through the atmosphere of the pressurized outer vessel into the retention chamber where they are held for a prescribed time.

The treatment liquor is an aqueous solution which facilitates, without removing substantial quantities of lignin, the defibration of wood chips into substantially undamaged fibers in the subsequent defibration step. It can be water or any suitable chemical solution commonly used to prepare thermomechanical, semi-chemical or chemi-mechanical high yield fibers. A preferred treatment liquor is one comprising as treating agents sodium sulfite and sodium bisulfite, each present at about from about 2% to about 6% by weight of dry pulp. Other suitable treatment liquors can contain as treating agents alkali metal sulfite, alkali metal bisulfite, sulfur dioxide in combination with alkali metal hydroxide, or mixtures thereof. The treatment liquor can optionally contain minor amounts of materials for penetration and mineral control.

Suitable treatment temperatures fall within the range of about 124° C. to about 190° C., preferably from about 125° C. to about 160° C. The pressure within the treatment unit is that stream pressure which corresponds to the temperature chosen.

The average residence time of a chip at elevated temperature in the retention chamber is from about 1 to about 60 minutes, preferably from about 1 to about 6 minutes.

When loblolly pine is used in this invention, the treatment liquor preferably comprises about 3% sodium sulfite and about 3% sodium bisulfite. The chips are preferably treated at a temperature of about 158° C. for about 5 minutes.

As indicated above, there is maintained in the impregnator an amount of treatment liquor sufficient to provide an excess of liquid when the chips are fully impregnated. The quantity of treatment liquor absorbed by the chips is dependent upon the species, the previous history of the chips, and the exact equipment and operating parameters used. Typically, for the equipment described above, the chips are impregnated with from about 30% to about 70% by weight treatment liquor based on the bone dry weight of the wood.

From the treatment unit, the treated wood chips pass to the defibration unit through the use of any suitable device such as a screw conveyor.

The defibrator can be any of the well known units used in the manufacture of theremomechanical or Asplund pulp. Specific examples are the Defibrator L-42 and the Asplund defibrators types OVP-20, RLP-50S, and RLP-54S. All of these units comprise one stationary disc and one rotating disc. Optionally, the defibration units can have two rotating disks. Disc designs can be any of those commonly used in the manufacture of theremomechanical or Asplund pulp.

Defibration is usually accomplished at from about 124° to about 160° C. at a consistency of about 25±5% by weight. Water or chemicals can be added to the treated chips immediately prior to their entry into or after their exit from the defibrator to adjust the consistency and to serve other purposes such as bleaching.

Power input to the defibrator is controlled, as by adjusting the clearance between the discs, so that the treated chips are defibrated to a pulp of acceptably high bulk while the level of shives is maintained at acceptably low levels. It is preferred that the fibers be left essentially intact and undamaged. When loblolly pine is used, and is treated as described hereinbefore, a power input of approximately 140 to about 450 kilowatt hours per metric ton is suitable.

From the defibrator, the pulp passes to a bleaching unit wherein it is bleached. Optionally, the bleaching step can be omitted at this point in the processing scheme, but it is then performed later after the softwood high yield fibers are mixed with the hardwood high yield fibers.

Any of the conventional bleaching processes well known to those skilled in the pulp art can be used. For example, hydrogen peroxide, sodium peroxide, or hydrosulfite can be used. Various bleaching systems are described in the *Bleaching of Pulp*, W. H. Rapson, Editor, TAPPI Monograph Series No. 27, (New York, 1963), which is incorporated herein by reference.

The fibers at this point in the process are presented as an aqueous slurry. They can either be directly incorporated in the form of this aqueous slurry into the furnish from which the dry sheets of this invention are made, or they may be dried by conventional bulk drying methods. In the latter situation they are redispersed in water as part of the sheet making process.

The softwood high yield fibers are relatively undamaged and substantially non-delignified. Relatively undamaged means that at least the majority of the individual fibers are rendered into pulp while retaining the length at which they were present in the raw wood and that at least the majority of the fibers do not present the typical appearance of fibers which have been mechanically refined. Substantially non-delignified means that associated with the fibers is a quantity of lignin substantially greater than that associated with those fibers from the same wood source which have been rendered into pulp by the conventional sulfite or kraft processes.

The Canadian standard freeness value (CSF) of the softwood high fibers useful in this invention is greater than about 700 ml. as determined according to T.A.P.-P.I. Method T-227 OS-58.

The second component of the sheets of this invention are high yield fibers prepared from hardwoods (angiosperms). Suitable hardwoods include, for example, alder, aspen, oak, and gum.

The high yield fibers prepared from hardwood are prepared in a manner analogous to that used for the softwood high yield fibers, but with significantly more stringent pretreating and defibrating conditions. The treatment liquor can contain as a treating agent alkali metal sulfite, alkali metal bisulfite, sulfur dioxide in combination with alkali metal hydroxide, or mixtures thereof. Sodium is the preferred alkali metal. The levels of treating agent in the treatment liquor can be from about 2% to about 40% by weight. The treatment liquor can optionally contain minor amounts of materials for penetration and mineral control. For example, when mixed hardwoods, predominately gum, are used, the treatment liquor preferably comprises from about 2% to about 20% by weight sodium sulfite and from about 2% to about 20% by weight sodium bisulfite. As above, the quantity of treatment liquor absorbed by the chips is dependent on many factors. Absorption levels of 100% or greater by weight of treatment liquor are possible. The chips are treated at about 130° to about 190° C. for from about 1 to about 60 minutes and are defibrated with a power input during defibration of from about 155 to about 500 kilowatt hours per metric ton of treated hardwood.

The hardwood high yield fibers can then be bleached in a bleaching unit as described above for softwood high yield fibers. Optionally, the bleaching step is omitted at this point in the processing scheme, but it is then performed later after the two types of high yield fibers are blended.

Canadian standard freeness (CSF) values of the hardwood high yield fibers are determined according to T.A.P.P.I. Method T-227 OS-58, which method is incorporated herein by reference. Preferably, the CSF of the hardwood high yield fibers used in this invention is between about 50 ml. and about 400 ml.

The softwood high yield fibers and the hardwood high yield fibers described above, bleached or optionally unbleached, are mixed in the wet state to prepare the papermaking furnish which will be used to form the sheets of this invention. While no special techniques or precautions are required in the mixing operation, which can be performed using equipment and techniques well known in the art, techniques which tend to retain any fines associated with the hardwood high yield fibers are preferred. There should be present in the furnish a major proportion of softwood high yield fibers and a minor proportion of hardwood high yield fibers. The weight ratio of softwood to hardwood high yield fibers should be from about 2.33:1 to about 19:1, preferably from about 5.67:1 to about 19:1.

If the two types of high yield fibers have not been bleached earlier in the processing scheme, they can be bleached after mixing. Any of the bleaching techniques described above can be used.

The slurry comprising the mixture of bleached softwood high yield fibers and bleached specially prepared hardwood high yield fibers is used as the furnish to form the sheets of this invention. Any of the various wet-forming techniques well known in the art for forming sheets of fibers can be used. Of particular usefulness are the various modifications of the well known Fourdrinier process. In general, this process involves adjusting the furnish to the appropriate consistency, applying the furnish to a moving foraminous surface such as a Fourdrinier wire, allowing excess water to drain from the fiber mat so formed through the foraminous surface, and subjecting the drained fiber mat to various pressing operations so as to expel more water. The coherent fibrous web is then dried by any convenient means such as a drying tunnel or rotating drum dryer. The dried sheet of fibers, which has significantly improved strength over an all-softwood high yield fiber sheet, is then cut into convenient sections or is wound upon a core to form a convenient sized roll.

Bursting Strength of the dried sheet is measured by T.A.P.P.I. Method T-403 OS-76, Tensile Strength by T.A.P.P.I. method T-404 OS-76, and Internal Tearing Resistance (Tear) by T.A.P.P.I method T-44 TS-65. All three methods are incorporated herein by reference. The thickness of a dried sheet is measured using a motorized micrometer which applies a load of 0.50 kg. per square centimeter using an anvil having a diameter of 1.60 centimeters.

The airfelts of this invention are prepared from the hereinbefore described sheets by a process comprising the steps of comminution, airlaying, and, optionally, compaction. Comminution (i.e. the mechanical separation of the sheets into essentially individual fibers) is accomplished by any of the equipment and processes well known in the art. Examples are found in U.S. Pat. No. 3,750,962 which was issued to Morgan on Aug. 7, 1973 and in U.S. Pat. No. 3,519,219 which was issued to Sakulich et al. on July 7, 1970 both of which are incorporated herein by reference. Following comminution, the separated high yield fibers are formed into a fibrous web by airlaying with equipment and processes common in the art. U.S. Pat. No. 3,772,739 which issued to Lovegrin on Nov. 20. 1973, incorporated herein by reference, illustrates a suitable airlaying process and provides a thorough discussion of airlaying technology. The airlaid web is optionally compressed by means well known in the art.

The apparent wet density of an airfelt is determined on a pad which has been compressed to a uniform density and which has been loaded with synthetic urine. The airfelt to be tested is prepared by airlaying 42 grams (dry basis) fiber as a 35.6 centimeter square pad. This pad is then cut into 10.2 centimeter square sections for testing. Any tissues on the sections are carefully removed. The section is compressed to such a thickness which will result, when the compressing load is removed, in an airfelt having a density of 0.10±0.01 gram per cubic centimeter. (Unless otherwise specified, when the thickness of an airfelt must be determined, as when densities are determined, the thickness is measured under a load of 12.4 grams per square centimeter). The densified section is placed on a planar surface and sprayed uniformly with a quantity of synthetic urine equal to three times the dry weight of the airfelt section. The wetted section is subjected to a loading of 2.2 grams per square centimeter. The load is removed and the section is subjected to a loading of 12.4 grams per square centimeter. The load is removed and the section is subjected to a loading of 35.2 grams per square centimeter. The load is removed and the section is allowed to recover for 60 seconds. The section is then subjected to a loading of 2.2 grams per square centimeter. The load is removed and the section is then subjected to a loading of 12.4 grams per square centimeter and the thickness of the section under this loading is recorded. The apparent wet density of the section is determined by dividing the dry weight of the section (in grams) by 104 times the last above measured thickness (in centimeters) of the section.

As used herein, synthetic urine is a 1% (weight) aqueous solution of sodium chloride which also contains 0.0025% octylphenoxy polyethoxy ethanol nonionic surfactant.

The wet burst strength of the airfelt is measured by determining the force required to rupture the sample used in the apparent wet density test with a rod provided with a 1.6 centimeter diameter spherical end, traveling at the rate of 12.7 centimeters per minute, while the sample is secured between plates having superimposed 6.35 centimeter-diameter orifices.

When intended for use in products such as disposable diapers, the airfelt has a basis weight of from about 240 to about 420 grams per square meter and a dry density of from about 0.08 to about 0.18 grams per cubic centimeter. Those skilled in the art can readily adjust these parameters to suit the particular end product use. Diapers can be made from the airfelt according to the teachings of U.S. Pat. No. Re. 26,151 which was issued to Duncan and Baker on Jan. 31, 1962 and which is incorporated herein by reference. Other absorbent products, such as sanitary napkins, incontinent pads, surgical bandages, and the like, can be prepared from the airfelts of this invention by means well known in the art.

As shown by the following example, one of the prominent features of the airfelt of this invention is its improved wet density property.

The following example is presented to more fully describe the invention disclosed herein and not by way of limitation.

EXAMPLE

Chips having a nominal length of 1.6 centimeters were prepared by standard techniques from debarked loblolly pine logs. These chips were used to make softwood high yield fibers by the techniques. and with the equipment hereinbefore described. The chips were heated in the presteamer to a temperature of 93° by the use of steam. From the presteamer, the heated chips were conveyed by a screw conveyor to the impregnator of the treatment unit where they were impregnated with a treatment liquor comprising 4.5% (weight) sodium sulfite, 4.5% sodium bisulfite and minor amounts of chemicals for mineral and penetration control. The chips retained 3% sodium sulfite and 3% sodium bisulfite. (The latter percentages are in terms of weight on the basis of oven dry wood.) The impregnated chips were removed from the impregnator by a screw conveyor and were allowed to fall through the atmosphere of the pressurized outer vessel to the retention chamber where they were retained for 5 minutes at 158° C. The impregnated, heated chips were conveyed by screw conveyor to an L-42 defibrator fitted with type 10782 plates. The chips were defibrated with a power input of 177 kilowatt hours per metric ton of pulp. Defibration was accomplished at 27% by weight consistency. The pH of the pulp exiting the defibrator was controlled.

The softwood high yield fibers were washed with softened water and were bleached with sodium peroxide using standard bleaching techniques. The bleaching solution comprised 6% (by weight) hydrogen peroxide, 5% 41° Be sodium silicate, 2% sodium hydroxide, 0.5% magnesium sulfate, and 0.15% DTPA. The bleaching was accomplished at a consistency of 12% in two hours at 82° C. The resulting pulp slurry was neutralized by the addition of sulfur dioxide. A second bleaching operation using 1% sodium hydrosulfite and 0.2% sodium tripolyphosphate was conducted at 3% consistency for 1 hour at 50° C. The resulting pulp had a CSF of about 750 milliliters.

Chips having a nominal length of 1.6 centimeters were prepared from debarked gum logs. Hardwood high yield fibers were prepared in the same equipment using the same techniques as were used to prepare the softwood high yield fibers with the exception that the chips were impregnated with a sufficient quantity of a treatment liquor comprising 7.8% (weight) sodium sulfite, 7.8% sodium bisulfite and a minor amount of mineral control agent to provide 10% sodium sulfite and sodium bisulfite. (The latter percentages are in terms of weight on the basis of oven dry wood.) The impregnated chips were held in the retention chamber for 30 minutes at 177° C. During defibrating, the power input was 296 kilowatt hours per metric ton. Following bleaching as immediately hereinbefore described the hardwood high yield fibers had a CSF of about 230 milliliters.

Blends of 10% (by weight), 15%, and 20% hardwood high yield fiber and, respectively, 90%, 85%, and 80% softwood high yield fiber were prepared and sheets were made on a conventional wet forming papermaking machine. It should be noted that skilled artisans were unable to prepare a sheet from a furnish comprising 100% of the softwood high yield fibers of this example. For comparison purposes, a control sheet was made from a blend of 90% of the above-described softwood high yield fiber and 10% northern kraft pulp refined to a CSF of approximately 270 milliliters. Also for comparison purposes, sheets were made from 100% chemical comminution grade pulp prepared from unrefined southern pine fibers.

The tests described above were conducted on the furnished sheets. In addition, airfelts were prepared by standard techniques from the sheets of fibers. The above described tests were used to evaluate the wet properties of these airfelts.

While the sheets having 10% and 15% hardwood high yield fiber were strong enough to be handled on commercial equipment, they exhibited slightly lower tensile strengths than the control sample. At the same time, they exhibited somewhat greater tear strength than did the control. The sheet containing 20% hardwood high yield fiber had greater tensile and tear strengths than did the control sheet.

Airfelts made from the sheets containing 10% and 15% hardwood high yield fiber had lower wet densities than did the airfelt made from the control sheet while the airfelt made from the sheet containing 20% hardwood high yield fiber had a slightly higher wet density when did the airfelt made from the control sheet. All three airfelts containing hardwood high yield fiber had wet burst strengths equivalent to the airfelt made from the control sheet.

As expected, sheets and airfelts made from conventional chemical comminution grade commercial pulp were stronger than any of those made from the softwood high yield fiber, but the airfelt made with the conventional pulp had a significantly higher wet density than did those made from the softwood high yield fiber.

It is contemplated that the sheets and airfelts of this invention will be comprised essentially or primarily of high yield fibers. It is within the scope of the invention, however, to incorporate quantities of chemical pulp into the sheets and into the airfelts. Quantities of chemical pulp up to about 25% by weight of total fiber can be incorporated into the sheets and into the airfelts. Fibers other than wood pulp fibers can also be incorporated into the sheets and airfelts of this invention, but such incorporation is, in general, not preferred.

What is claimed is:

1. A process for preparing sheets of high yield wood pulp fibers comprising the steps of:
   (A) providing substantially non-delignified and relatively undamaged softwood high yield fibers having a Canadian standard freeness value greater than about 700 ml;
   (B) providing hardwood high yield fibers wherein said hardwood fibers:
      (i) have a Canadian standard freeness value of from about 50 ml to about 400 ml;
      (ii) have been prepared separately from said softwood fibers; and
      (iii) have been prepared by a process comprising the steps of:
         (a) treating hardwood with an aqueous solution comprising from about 2% to about 40% by weight of a treating agent selected from the group consisting of alkali metal sulfite, alkali metal bisulfite, sulphur dioxide with alkali metal hydroxide, and mixtures thereof at a temperaure of from about 130° C. to about 190° C. for from about 1 minute to about 60 minutes; and
         (b) defibrating said treated hardwood;
   (C) mixing said softwood and hardwood fibers to form a papermaking furnish comprising at least about 75% by weight said softwood and hardwood fibers and wherein the weight ratio of said softwood fibers to said hardwood fibers is from about 2.33:1 to about 19:1; and
   (D) wet forming said sheets from said papermaking furnish.

2. The process of claim 1 wherein the weight ratio of said softwood fibers to said hardwood fibers is from about 5.67:1 to about 19:1.

3. The process of claim 1 or 2 wherein the power input during said defibrating step is from about 155 to about 500 kilowatt hours per metric ton of treated hardwood.

4. The process of claim 1 or 2 wherein said aqueous solution comprises from about 2% to about 20% by weight sodium sulfite and from about 2% to about 20% by weight sodium bisulfite.

5. The process of claim 4 wherein the power input during said defibrating step is from about 155 to about 500 kilowatt hours per metric ton of treated hardwood.

6. The wet formed sheet of the process of claims 1 or 2.

7. The wet formed sheet of the process of claim 3.

8. The wet formed sheet of the process of claim 3.

9. The wet formed sheet of the process of claim 5.

10. A process for preparing airfelts comprising the steps of:
    (A) comminuting sheets of high yield wood pulp fibers; and
    (B) airlaying said comminuted high yield wood pulp fibers wherein:
       (i) said sheets of high yield wood pulp fibers comprise at least about 75% by weight substantially non-delignified and relatively undamaged softwood high yield fibers and hardwood high yield fibers and wherein the weight ratio of said softwood fibers to said hardwood fibers is from about 2.33:1 to about 19:1;
       (ii) said softwood high yield fibers have a Canadian standard freeness value greater than about 700 ml;
       (iii) said hardwood high yield fibers:
          (a) have a Canadian standard freeness value of from about 50 ml to about 400 ml; and
          (b) have been prepared by a process comprising the steps of:
             (aa) treating hardwood with an aqueous solution comprising from about 2% to about 40% by weight of a treating agent selected from the group consisting of alkali metal sulfite, alkali metal bisulfite, sulphur dioxide with alkali metal hydroxide, and mixtures thereof at a temperature of from about 130° C. to about 190° C. for from about 1 minute to about 60 minutes; and
             (bb) defibrating said treated hardwood.

11. The process of claim 10 wherein the weight ratio of softwood fibers to hardwood fibers is from about 5.67:1 to about 19:1.

12. The process of claims 10 or 11 wherein the power input during said defibrating step is from about 155 to about 500 kilowatt hours per metric ton of treated hardwood.

13. The process of claims 10 or 11 wherein said aqueous solution comprises from about 2% to about 20% by weight sodium sulfite and from about 2% to about 20% by weight sodium bisulfite.

14. The process of claim 13 wherein the power input during said defibrating step is from about 155 to about 500 kilowatt hours per metric ton of treated hardwood.

15. The airfelt of the process of claims 10 or 11.

16. The airfelt of the process of claim 12.

17. The airfelt of the process of claim 13.

18. The airfelt of the process of claim 14.

* * * * *